(12) United States Patent
Stone

(10) Patent No.: US 6,391,864 B1
(45) Date of Patent: May 21, 2002

(54) FOOD SUPPLEMENT CONTAINING A CARTILAGE SUPPLEMENT

(75) Inventor: Kevin Stone, Mill Valley, CA (US)

(73) Assignee: Joint Juice, Inc., San Francisco, CA (US)

(*) Notice: Subject to any disclaimer, the term of this patent is extended or adjusted under 35 U.S.C. 154(b) by 0 days.

(21) Appl. No.: 09/338,021

(22) Filed: Jun. 22, 1999

Related U.S. Application Data

(60) Provisional application No. 60/097,038, filed on Aug. 19, 1998.

(51) Int. Cl.$^7$ .................. A61K 31/70; A61K 31/22; A61K 35/00; A61K 38/00; A23L 2/00

(52) U.S. Cl. .................. 514/62; 424/439; 424/764; 426/590; 426/599; 426/601; 426/611; 426/612; 426/648; 426/655; 426/656; 426/658; 514/2; 514/23; 514/25; 514/54; 514/546; 514/549; 514/552

(58) Field of Search .................. 424/439, 440, 424/600, 195.1; 514/2, 23, 25, 54, 62, 492, 546, 549, 552; 426/74, 590, 593, 599, 631, 512, 72, 601, 611, 648, 655, 656, 658

(56) References Cited

U.S. PATENT DOCUMENTS

| | | | | |
|---|---|---|---|---|
| 3,679,660 A | | 7/1972 | Magnus | 536/54 |
| 4,108,849 A | * | 8/1978 | Thomas | 530/395 |
| 4,466,958 A | * | 8/1984 | Morrison | 424/724 |
| 4,647,453 A | | 3/1987 | Meisner | 424/54 |
| 4,766,209 A | | 8/1988 | Chen et al. | 536/55.3 |
| 5,569,676 A | * | 10/1996 | Diehl | 514/549 |
| 5,587,363 A | * | 12/1996 | Henderson | 514/54 |
| 5,629,411 A | * | 5/1997 | Ishiguro et al. | 536/18.1 |
| 5,796,576 A | * | 8/1998 | Diaz et al. | 424/195.1 |
| 5,843,919 A | | 12/1998 | Burger | 514/62 |

FOREIGN PATENT DOCUMENTS

| | | |
|---|---|---|
| EP | 0 223 540 A2 | 5/1987 |
| EP | 0 587 972 A1 | 3/1994 |
| EP | 0 744 902 B1 | 10/1997 |
| JP | 62224268 | 10/1987 |
| WO | WO 97/49304 | 12/1997 |
| WO | WO 00/78320 A1 | 12/2000 |

OTHER PUBLICATIONS

ACC.97: 271462 NLDB, Abstract, "Arthred–G Powdered Dietary Supplement—Hydrolyzed." (1997).
Lauscher, "Compositions for the treatment of degenerative joint diseases", Patent No. DE2103387, 1972, abstract.
International Search Report (2001), International Application No. PCT/US00/40267.
Integris Dietary Supplement—EverLasting Capsules (Product Alert, Dec. 22, 1997), STN/CAS online, file PROMT abstract.*
Dr. Atkins' Vita–Nutrient Solution:Nature's Answers to Drugs (Feb. 2, 1998), pp. 221, 222, 272–75.*
Simandi et al. The effect of cetyl myristoleate and adjunctive therapy on the course of arthritic episodes in patients with various auto–immune diseases characterized by the common terminology, "arthritis" and "psoriasis" (1977) (http://www.sierranatural.com/docs/siemandi.htm) pp. 1–8.*

* cited by examiner

*Primary Examiner*—Jose G. Dees
*Assistant Examiner*—Frank Choi
(74) *Attorney, Agent, or Firm*—McDermott, Will & Emery

(57) ABSTRACT

The present invention relates to a food supplement, either in the form of a snack bar or a beverage, which contains cartilage supplements. The cartilage supplements include chondroitin sulfate, glucosamine sulfate, and hyaluronic acid. The food supplement may additionally be fortified with cetyl myristoleate.

14 Claims, No Drawings

FOOD SUPPLEMENT CONTAINING A CARTILAGE SUPPLEMENT

REFERENCE TO RELATED APPLICATIONS

This application is related to U.S. Provisional Patent Application Serial No. 60/097,038, filed Aug. 19, 1998.

FIELD OF THE INVENTION

The present invention relates to food supplements, such for example, high energy snack bars and beverages which are fortified with cartilage supplements and which can be additionally fortified with cetyl myristoleate.

BACKGROUND

Nutritional bars and energy drinks are convenient nutritional supplements, particularly for those persons too busy to eat regular meals and for hikers, cyclists, runners or other athletes who need prepackaged, ready-to-eat, high-energy snacks while they are exercising. Such bars and drinks are also convenient nutritional supplements for the elderly who need prepackaged, ready-to-eat snacks. Additionally, such food supplements can supply consumers with the necessary vitamins and minerals specified in the recommended daily allowances provided by the U.S. government.

By way of example, U.S. Pat. No. 4,543,262 discloses a high protein, low or no lactose, vitamin and mineral fortified, nutritionally-balanced snack bar. Additionally, U.S. Pat. No. 3,814,819 teaches a protein-fortified food bar composed of several baked crisp wafers layered on top of the other with a creamy filling between them. The creamy filling contains added vitamins, providing twenty-five percent (25%) of the recommended daily allowance of vitamins and minerals. U.S. Pat. No. 4,152,462 teaches a highly nutritious protein and vitamin enriched food bar, having a marshmallow base. Lastly, U.S. Pat. No. 3,901,799 discloses a high protein chocolate bar. Caseinate and peanut butter are added to a mixture of chocolate and cocoa butter. Vitamins compatible with the ingredients, it is disclosed, can be added to the snack bar.

Drinks formulations and methods for preparing them have also been developed. Energy enhancement drinks and processes have been developed such as in U.S. Pat. No. 3,894,148, which relates to nutritional and exercise therapy to maximize the storage of glycogen in muscle tissue. Protein fortification drinks have been described in U.S. Pat. No. 4,309,417. Finally, carbohydrate and electrolyte drinks have been described in U.S. Pat. Nos. 4,312,856 and 4,322,407.

It has been long recognized that dietary cartilage supplements are effective in reducing the symptoms of joint pain. (Drovani, Clinical Therapeutics, (1980)). An amino-acid complex combining glutamine with glucosamine sulfate is the constituent component used by the body to make cartilage and connective tissue, which cushion and lubricate the joints in the body. To date, more than 6,000 patients have been studied in 20 clinical trials. These studies have all reached the conclusion that glucosamine sulfate supplements relieve pain and stimulate healing in osteoarthritis patients. In fact, the World Health Organization has officially classified glucosamine sulfate as a slow-acting drug for the treatment of osteoarthritis. Typically, glucosamine sulfate is taken in the form of a pill or a powder.

Chondroitin sulfate is another compound widely sold as an agent for the treatment of the symptoms of joint pain. Its healing properties as a dietary supplement, however, while still effective, have proven in two studies to be lower than the healing properties of glucosamine sulfate. Chondroitin sulfate is also taken in the form of a pill or a powder.

Hyaluronic acid is a polysaccharide which forms a major component of the gel-like substance found in the connective tissue of mammals. Structurally, it is comprised of a repeating disaccharide consisting of N-acetyl-D-glucosamine and D-glucuronic acid. Functionally, it serves as a lubricant and shock absorbent in mammalian joints. Hyaluronic acid is also taken in the form of a pill or a powder and is thought to be effective for the treatment of joint pain.

Cetyl myristoleate (CM) is a newly recognized agent that is potentially useful for the treatment of joint pain. CM is an ester of a fatty acid, the building blocks of fats and oils. CM is produced by combining the fatty acid myristolic acid with cetyl alcohol, a long-chain alcohol. CM appears to function in three ways in the body. First, it shows an anti-inflammatory effect. Second, it appears to act as a lubricant for joints. Third, CM functions as an immune system modulator.

Doctors have reported that significant improvement in patients with osteoarthritis who were taking CM. In 1996, in a one-month multi-center clinical study involving 431 patients with various forms of arthritis, sixty-three percent (63%) of those taking CM showed improvement compared to fourteen percent (14%) in the control group. CM is typically taken orally in the form of an oil.

Konjac flour is a soluble dietary fiber that is similar in structure and function to pectin and typically is used as a thickener, emulsifier, gelling agent, film former and stabilizer. Glucomannan, the main constituent of Konjac flour, is a slightly branched hydrocolloidal polysaccharide having B1–4 linked subunits of glucose and mannose and having a molecular weight ranging between 200,000 and 2,000,000 daltons. Acetyl groups, located every 9–19 subunits along the glucomannan backbone, help solubilize the molecule. In addition to being a food agent, glucomannan has been tested on humans, principally as a means for lowering serum cholesterol, bile acid level and serum triglyceride. Studies indicate that glucomannan may affect glucose tolerance and glucose absorption.

Stevia (*Stevia rebaudiana bectoni*) is a natural, non-caloric sweet-tasting plant that is typically used in medical applications for inhibiting fat absorption and for lowering blood pressure as well as in the food industry as a non-caloric sweetening agent. Stevioside is the component of Stevia that gives the plant its sweetness. As a sugar substitute, it is available as a concentrated liquid, crushed leaf, or concentrated white powder. Often, individuals who do not tolerate sugar or other sweeteners can use Stevia. Medicinally, studies indicate that Stevia helps regulate the pancreas and may help stabilize blood sugar levels within the body. Stevia is also indicated as a cardiotonic, for obesity, to reduce stomach acidity, to reduce gas, for hypotension and to help lower uric acid levels. Research has also indicated that Stevia may help reduce bacteria.

While carbohydrates, proteins and fats are all important in the human diet, carbohydrates are particularly important for athletic performance. Carbohydrates are a well-known source of energy which are readily absorbed by the body. For example, marathon runners and other athletes typically "carbo-load" the day before a race by eating large amounts of carbohydrates. Moreover, athletes in endurance events need a source of energy which is readily absorbable by the body in order to replace the diminishing stores of glucose and glycogen that occur during the event. Lastly, athletes typically consume large quantities of carbohydrates immediately following a race in order to replenish glycogen levels depleted by the event. Thus, the energy source provided by carbohydrates is important to athletes before, during, and after the race.

Typically, carbohydrates range between complex carbohydrates and simple sugars. Structurally, these carbohydrates differ in the number of sugars in the molecule and in the degree of branching. Functionally, they differ by how readily the body can absorb them and process them to derive energy. Thus, the correct ratio of the different types of carbohydrates can supply short-term, mid-term, and long-term supplies of energy to the body.

During athletic events, particularly endurance events such as marathon running, triathalons and long distance cycling, athletes can deplete much, if not all, of their glycogen stores. It is therefore important that athletes replenish their depleted stores of glycogen from a source of carbohydrates. Typically, the cellular machinery used to convert glucose to glycogen is most efficient in the several hours immediately following the athletic event, the so-called recovery period. In addition to depleting their glycogen stores, athletes can cause temporary, and sometimes permanent, damage to the joints of their bodies. Typically, they experience this damage as pain and stiffness in their joints. The present invention provides a quality source of carbohydrates, which is important during the recovery period. The invention also provides supplements for the carbohydrate source. These supplements include one or more cartilage supplements which also aid in recovery by reducing joint pain and stiffness, and/or Konjac flour and/or Stevia supplements. The supplements are provided alone or in combination with CM.

It is therefore one object of this invention to provide a formula which provides a nutritional snack together with cartilage supplements which address cartilage dysfunction, and/or a Konjac flour supplement and/or a Stevia supplement.

It is another object of the invention to provide a formula which provides a nutritional snack together with cartilage supplements which address cartilage dysfunction, and/or a Konjac flour supplement and/or a Stevia supplement, in combination with CM.

It is yet another object of this invention to provide a nutritional snack which aids athletes in recovering from athletic events.

SUMMARY OF THE INVENTION

The present invention provides a nutritional food supplement. The food supplement can be either in the form of a beverage or a snack bar. The food supplement disclosed by the present invention is fortified with one or more cartilage supplements including glucosamine sulfate, chondroitin sulfate and hyaluronic acid. The food supplements disclosed by the invention are also fortified with Konjac flour and/or Stevia supplements either alone or in combination with the cartilage supplements. The food supplement, as disclosed by the invention, can be optionally further fortified with cetyl myristoleate (CM).

In one preferred embodiment, the present invention provides a high protein, nutritional snack bar that is fortified with one or more cartilage, Konjac flour and/or Stevia supplements, and which can also be fortified with CM. The snack bar has pleasing textural and taste characteristics. In another preferred embodiment, the present invention provides a beverage which is fortified with one or more cartilage, Konjac flour and/or Stevia supplements, and which can be additionally fortified with CM.

All of the compounds used to fortify the food supplement, according to the present invention, are safe for human consumption. Moreover, while sulfate is the preferred counter ion for chondroitin and glucosamine, any counter ion which is safe for human consumption is suitable for use in the present invention.

In one preferred embodiment, the food supplement containing the cartilage, Konjac flour and/or Stevia supplements, alone or in combination with CM, is a nutritional snack bar. The process of preparing the snack bar, according to the present invention, comprises melting a confectioner's material, which is a solid at ambient temperature. The melted confectioner's material is admixed with the major liquid ingredients and with the major and minor dry ingredients. If the snack bar, according to the present invention, is to be fortified with CM, the CM is first admixed with the major liquid ingredients. Admixing the minor dry compounds with the major liquid ingredients prior to admixing with the confectioner's material minimizes localized concentrations of dry ingredients.

The above mixture is extruded in an extruder typical of extruders known to those skilled in the art. The extruded material or extrudate is then cut to a desired size. The snack bar can be coated on the surface with a melted confectioner's coating material and/or a topping to enhance taste and visual appeal.

In another preferred embodiment, the above-referenced snack bar is modified to include one or more reservoirs, each reservoir containing cartilage, Konjac flour and/or Stevia supplements or mixtures of two or more of such supplements. Within each reservoir, the supplements can be further combined with CM. By way of example, the snack bar can contain a substance such as chocolate or carob, which is molded with one or more internal void regions or reservoirs.

In another preferred embodiment, the cartilage, Konjac flour and/or Stevia supplements and the CM are provided in the form of a beverage. Beverages suitable for use in the present invention include fruit juices, commercially available sports drinks such as GATORADE and POWERADE, and commercially available nutritionally-balanced beverages such as ENSURE.

DETAILED DESCRIPTION OF THE PREFERRED EMBODIMENTS

Commercially available confectioner's coating material is used in the present invention. The compositions of typical confectioner's coating materials which can be used in the present invention, are disclosed in cookie and cracker technology, A VI Publishing Co., Westport, Conn., page 176, table 45 (1968). These materials are generally solid at room temperature, but melt and can be poured when heated. The confectioner's material in the present invention preferably has melting points below 140° F. and more preferably below 105° F.

Confectioner's material with higher melting or pouring points can present several difficulties. For example, the higher the melting point of the coating material, the greater is the risk that the heated coating material will begin to set or partially solidify when admixed with the other ingredients that are preferably maintained at room temperature. Premature hardening of the coating material can cause a lack of uniform distribution of the confectioner's material within the snack bar. As a result, any ingredients added to the confectioner's material may also not be uniformly distributed throughout the product. This is particularly true of flavoring ingredients which may be added to the melted confectioner's material.

In the present invention, the confectioner's coating material may be cocoa butter-based or alternatively may be a compound coating, which is made from hardened vegetable oils. Examples of hardened vegetable oils used for compound coatings include cottonseed, coconut, soybean, palm and peanut oils. These hardened vegetable oils are mixed with sugar and are the principle ingredients in the coating material. Compound coatings may be peanut flavored, fruit flavored, chocolate flavored, vanilla flavored, coconut flavored or flavored with other commercially available flavorings.

The snack bar according to the present invention, can be fortified with protein from several sources of edible protein, either alone or in combination. Exemplary sources include whey powder, carob powder, soy lecithin, peanut flour, wheat proteins such as wheat germ and caseinates such as calcium, potassium and sodium caseinates.

Exemplary sources of carbohydrates suitable for the snack bar of the present invention include malted cereal syrup from corn, barley and brown rice; maltodextran; fructose; high fructose corn syrup; date paste; sucrose; brown sugar and mixtures thereof. Exemplary sources of complex carbohydrates include those derived from cereal grains such as oats, rice, barley, and corn. Preferably, the snack bar according to the present invention, contains at least one sugar and at least one cereal grain as the sources of carbohydrates.

In the present invention, corn syrup, preferably high fructose corn syrup, is used as a source of carbohydrates. The corn syrup gives the snack a moist chewy texture, provides a source of sweetness to the snack bar, and aids in distributing the dry ingredients. Additionally, the corn syrup together with the confectioner's coating material, binds together the other ingredients such as the protein source ingredients and the cereal grain ingredients.

Fats have the highest source of energy per unit weight, approximately twice that of proteins or carbohydrates. In addition to the confectioner's coating material, other sources of fat suitable for use in the present invention include flavoring such as chocolate, cocoa, and coconut and at least one partially hydrogenated vegetable oil such as soybean, cottonseed, corn and palm oil.

The above-listed ingredients are categorized based on the main nutritional component that each contributes to the snack bar. It is, however, useful to note that many of the ingredients may be sources of two or more nutritional components. For example, whey powder, peanut flour, and wheat germ each contain substantial amounts of carbohydrates, proteins, and fats. By varying the ingredients in the snack bar, one can maintain the caloric distribution disclosed by the present invention.

Several additional ingredients are preferably added to the snack bar according to the present invention. For example, the snack bar may be topped with conventional toppings such as crushed nuts, granola and the alike. Additionally, although shortenings other than the confectioner's coating are not necessary, it is preferable to include a wetting agent to facilitate mixing and binding of the dry ingredients with the confectioner's coating and corn syrup and to enhance the moisture and chew capability of the snack. Suitable wetting agents for use in the present invention include molasses, honey, and the partially hydrogenated vegetable oils.

The nutritional snacks according to the present invention, are made by first melting the confectioner's coating material by heating it to its melting point or to within about ten degrees (10°) Fahrenheit above its melting point. Next, the liquid ingredients which comprise the corn syrup, the melted confectioner's coating material, and the optional wetting agent are mixed together. If the snack bar is to be fortified with cetyl myristoleate (CM), the CM is added to the liquid ingredients. The liquid ingredients are mixed to substantial homogeneity.

Once the liquid ingredients are thoroughly mixed, the minor dry ingredient are mixed into the liquid ingredients. The minor dry ingredients include the chondroitin sulfate, the glucosamine sulfate, the hyaluronic acid and the optional salt. The minor dry ingredients are mixed with the liquids in order to avoid localized high concentrations of the minor dry ingredients.

Once the minor dry ingredients are mixed to substantial homogeneity with the liquid ingredients, the major dry ingredients are then admixed to the liquid ingredients and the minor dry ingredients. This mixture is mixed to substantial homogeneity. Major dry ingredients include the high content carbohydrates such as sugars and cereal grains and the high content proteins such as the whey protein, soy protein, peanut protein and caseinate.

Flavoring ingredients such as cocoa or coconut can be added to the mixture. When adding flavoring ingredients, it is preferable to add them to the liquid ingredients to avoid localized concentrations within the snack bar. Once all the ingredients are mixed to substantial homogeneity, the mixture is transferred to a conventional confectionary-type bar extruder. The mixture is forced through a die of the extruder to form the extrudate. The die may be any shape known to those skilled in the art, but is preferably rectangular. The extrusion is done at room temperature.

After extrusion, the extrudate is cut to the desired size. The cut extrudate may then be coated by, for example, dipping with a melted confectioner's coating material. The bar is then chilled and may then be topped with a topping such as granola or ground nuts. The bar is then packaged for shipping or storage.

EXAMPLE 1

In this example, a snack bar with a surface coating is prepared. The ingredients and relative amounts are:

| INGREDIENTS | PERCENTAGE TOTAL WEIGHT |
| --- | --- |
| Whey Protein | 24.5 |
| Sugars | 8.0 |
| Rice Flour | 16.0 |
| Soy Protein | 6.0 |
| Chondroitin Sulfate | 1.5 |
| Glucosamine Sulfate | 1.5 |
| Hyaluronic Acid | 1.5 |
| Salt | 0.5 |
| Corn Syrup | 28.5 |
| Molasses | 4.0 |
| Confectioner's Peanut Butter | 8.0 |
| TOTAL | 100.0 |

The snack bar of the present invention is made by melting the confectioner's peanut butter material and mixing in a conventional mixer, the liquid components which comprise the high fructose corn syrup and the molasses.

The second step is to add the minor dry ingredients comprising the salt, chondroitin sulfate, glucosamine sulfate and the hyaluronic acid, to the liquid mixture. The mixture is mixed to substantial homogeneity.

The third step in the process is adding the major dry ingredients to the mixed ingredients of the second process step. The major dry ingredients include the sugars, whey protein, rice flour and soy protein. The mixture is then mixed to substantial homogeneity. The mixture is then fed into a conventional extruding machine.

The mixture is extruded at room temperature. As the mixture is extruded, the extrudate is cut into individual serving sizes of about sixty (60) grams. The cut pieces are then coated with approximately ten (10) grams of melted chocolate confectioner's material. The bar is then allowed to cool or is chilled and is wrapped for shipping and storage. The final bar is approximately seventy (70) grams and has bout three hundred (300) calories.

EXAMPLE 2

A nutritional bar with a core, a surface coating and a topping is prepared. The bar is further fortified with CM. The ingredients and relative amounts are as follows:

| INGREDIENTS | PERCENTAGE BASED ON WEIGHT |
| --- | --- |
| Bran | 2.5 |
| Oat | 10.0 |
| Barley | 4.0 |
| Fructose | 6.0 |
| Caseinate | 11.0 |
| Flavorings | 4.0 |
| Wheat Germ | 13.0 |
| Chondroitin Sulfate | 1.5 |
| Glucosamine Sulfate | 1.5 |
| Hyaluronic Acid | 1.5 |
| Salt | 0.5 |
| Corn Syrup | 25.0 |
| Partially Hydrogenated Vegetable Oil | 1.0 |
| Cetyl Myristoleate (CM) | 1.5 |
| Chocolate Confectioner's Compound Coating | 18.5 |
| TOTAL | 100.0 |

The snack bar is made by melting chocolate confectioner's coating material. The corn syrup, vegetable oil and CM are next added to the melted confectioner's coating.

Next, the minor dry ingredients, as set forth in Example 1, are mixed with the liquids, along with the flavorings. The mixture is mixed to substantial homogeneity.

To this mixture, the major dry ingredients are then added. These include the bran, oats, barley, fructose, caseinate, and the wheat germ. The mixture is then mixed to substantial homogeneity.

The mixture is then processed as set forth in Example 1. The bar is then coated with approximately ten (10) grams of melted chocolate confectioner's's coating and then topped with crushed nuts. The bar is then packaged for shipping and storage.

In another preferred embodiment, the cartilage supplements, either alone or in combination with, the CM are supplied in the form of a beverage. By way of non-limiting example, beverages suitable for use in the present invention include fruit juices such as apple juice, orange juice, grapefruit juice, cranberry juice, pineapple juice, grape juice, and mixtures thereof. Other beverages suitable for use in the present invention include commercially available sports drinks such as GATORADE and POWERADE. Generally, these sports drinks provide calories substantially only in the form of carbohydrates and provide electrolyte replacements, which are thought to aid in recovery after exercise. Lastly, commercially available nutritionally balanced beverages, such for example ENSURE, are suitable for use in the present invention. These nutritionally balanced beverages generally provide carbohydrates, protein, fat, vitamins and minerals to consumers and often serve as meal replacements.

All three cartilage supplements, either alone or in combination, can be added to the above-identified beverages. The cartilage supplement may be in a particulate form adapted for suspension or solution in a fluid carrier. The fluid carrier may be a fruit juice or a mixture of fruit juices. It is important to note, however, that CM is an oily-like substance and, therefore, tends not to be readily miscible with the aqueous based beverages. Accordingly, when CM is added to a beverage according to the present invention, it must first be emulsified. Emulsifying agents and methods known to those skilled in the art are suitable for use in the present invention. The emulsifying agent chose must fit for human consumption. Suitable emulsifying agents include gum arabic and gelatin. The emulsions are prepared by shaking together the two liquids or by adding one phase drop-wise to the other with some form of agitation, such as irradiation by high intensity ultrasonic waves.

EXAMPLE 3

The beverage of the present invention containing the cartilage supplements is produced as follows:

First, a volume of GATORADE is aliquoted into a conventional fluid mixer. Hyaluronic acid, glucosamine sulfate, and chondroitin sulfate are next added to the solution to a final concentration of four percent (4%) (weight to volume) of each component. The solution is next mixed until the added ingredients become solubilized. The solution is then aseptically filled into individual serving size bottles of approximately five hundred milliliters (500 ml).

EXAMPLE 4

The beverage of the present invention containing the cartilage supplement and the CM is produced as follows:

First, CM is emulsified with any known emulsifying agent suitable for human consumption. Next, a volume of ENSURE is aliquoted into a conventional fluid mixer. The emulsified CM is added to a final concentration of two percent (2%) (volume to volume). Next, the hyaluronic acid, glucosamine sulfate, and chondroitin sulfate are added to the solution to a final concentration of four percent (4%) (weight to volume). The solution is mixed until the added cartilage supplements become solubilized. The solution is then aseptically filled into individual serving size bottles of approximately five hundred milliliters (500 ml).

Those of skill in the art will recognize that the invention may be embodied in other specific forms without departing from the spirit of essential characteristics thereof. The presently described embodiments are therefore to be considered in all respects as illustrative and not restrictive, the scope of the invention being indicated by the appended claims rather than by the foregoing description. All changes that come within the meaning and range of the equivalency of the claims are therefore intended to be embraced therein.

What is claimed is:

1. A food supplement consisting of at least one cartilage enhancing supplement, emulsified cetyl myristoleate, stevia, and at least one energy source selected from the group consisting of fats, carbohydrates, protein, and combinations thereof, and a beverage base, wherein the cartilage enhancing supplement is glucosamine in association with a counter ion and said beverage base is at least in part a fruit juice or fruit flavored juice.

2. A food supplement according to claim 1 wherein the counter ion is sulfate.

3. A food supplement consisting of at least one cartilage enhancing supplement, emulsified cetyl myristoleate, stevia, and at least one energy source selected from the group consisting of fats, carbohydrates, protein, and combinations thereof, and a beverage base, wherein the cartilage enhancing supplement is glucosamine, and said beverage base is at least in part a fruit juice or fruit flavored juice, wherein the emulsified cetyl myristoleate is emulsified by:
   a. combining the cetyl myristoleate with an emulsifying agent; and
   b. mixing the cetyl myristoleate and the emulsifying agent.

4. A food supplement consisting of at least one cartilage enhancing supplement, emulsified cetyl myristoleate, stevia, and at least one energy source selected from the group consisting of fats, carbohydrates, protein, and combinations thereof, and a beverage base, wherein the cartilage enhancing supplement is glucosamine, and said beverage base is at least in part a fruit juice or fruit flavored juice, wherein the glucosamine is in a particulate form adapted for suspension or solution in a fluid carrier.

5. A food supplement consisting of at least one cartilage enhancing supplement, emulsified cetyl myristoleate, and at least one energy source selected from the group consisting of fats, carbohydrates, protein, and combinations thereof, and a beverage base, wherein the cartilage enhancing supplement is glucosamine in association with a counter ion, and said beverage base is at least in part a fruit juice or fruit flavored juice.

6. A food supplement according to claim 5 wherein the counter ion is sulfate.

7. A food supplement consisting of at least one cartilage enhancing supplement, stevia, and at least one energy source selected from the group consisting of fats, carbohydrates, protein, and combinations thereof, and a beverage base, wherein the cartilage enhancing supplement is glucosamine in association with a counter ion, and said beverage base is at least in part a fruit juice of fruit flavored juice.

8. A food supplement according to claim 7 wherein the counter ion is sulfate.

9. A food supplement consisting of at least one cartilage enhancing supplement, emulsified cetyl myristoleate, stevia, and at least one energy source selected from the group consisting of fats, carbohydrates, protein, and combinations thereof, and a beverage base, wherein the cartilage enhancing supplement is glucosamine, and said beverage base is at least in part a fruit juice or fruit flavored juice, wherein the emulsified cetyl myristoleate is emulsified by:
   a. combining the cetyl myristoleate with an emulsifying agent; and
   b. mixing the cetyl myristoleate and the emulsifying agent.

10. A food supplement consisting of at least one cartilage enhancing supplement, emulsified cetyl myristoleate, stevia, and at least one energy source selected from the group consisting of fats, carbohydrates, protein, and combinations thereof, and a beverage base, wherein the cartilage enhancing supplement is glucosamine, and said beverage base is at least in part a fruit juice or fruit flavored juice.

11. A food supplement consisting of at least one cartilage enhancing supplement, emulsified cetyl myristoleate, and at least one energy source selected from the group consisting of fats, carbohydrates, protein, and combinations thereof, and a beverage base, wherein the cartilage enhancing supplement is glucosamine, and said beverage base is at least in part a fruit juice or fruit flavored juice.

12. A food supplement consisting of at least one cartilage enhancing supplement, stevia, and at least one energy source selected from the group consisting of fats, carbohydrates, protein, and combinations thereof, and a beverage base, wherein the cartilage enhancing supplement is glucosamine, and said beverage base is at least in part a fruit juice or fruit flavored juice.

13. A food supplement consisting of at least one cartilage enhancing supplement, emulsified cetyl myristoleate, and at least one energy source selected from the group consisting of fats, carbohydrates, protein, and combinations thereof, and a beverage base, wherein the cartilage enhancing supplement is glucosamine, and said beverage base is at least in part a fruit juice or fruit flavored juice, wherein the glucosamine is in a particulate form adapted for suspension or solution in a fluid carrier.

14. A food supplement consisting of at least one cartilage enhancing supplement stevia, and at least one energy source selected from the group consisting of fats, carbohydrates, protein, and combinations thereof, and a beverage base, wherein the cartilage enhancing supplement is glucosamine, and said beverage base is at least in part a fruit juice or fruit flavored juice, wherein the glucosamine is in a particulate form adapted for suspension or solution in a fluid carrier.

* * * * *